US012644094B2

(12) United States Patent　　　　(10) Patent No.:　US 12,644,094 B2
Duboux et al.　　　　　　　　　　　 (45) Date of Patent:　　　Jun. 2, 2026

(54) SERPIN PRODUCTION

(71) Applicant: SOCIETE DES PRODUITS NESTLE S.A., Vevey (CH)

(72) Inventors: Stephane Duboux, St-Prex (CH);
　　　　　　 Mireille Golliard, Lausanne (CH);
　　　　　　 Michiel Kleerebezem, Wageningen (NL)

(73) Assignee: Societe des Produits Nestle S.A.,
　　　　　　　Vevey (CH)

( * ) Notice: Subject to any disclaimer, the term of this
　　　　　　 patent is extended or adjusted under 35
　　　　　　 U.S.C. 154(b) by 563 days.

(21) Appl. No.: 17/597,306

(22) PCT Filed: Jun. 30, 2020

(86) PCT No.: PCT/EP2020/068400
　　　§ 371 (c)(1),
　　　(2) Date: Dec. 31, 2021

(87) PCT Pub. No.: WO2021/001368
　　　PCT Pub. Date: Jan. 7, 2021

(65) Prior Publication Data
　　　US 2022/0315883 A1　　Oct. 6, 2022

(30) Foreign Application Priority Data
　　　Jul. 1, 2019　(EP) .................................... 19183653

(51) Int. Cl.
　　　*C12N 1/20*　　　(2026.01)
　　　*A61K 31/7016*　(2006.01)
　　　*A61K 35/745*　(2015.01)
　　　*C12R 1/01*　　(2006.01)
　　　*A61K 35/00*　(2006.01)

(52) U.S. Cl.
　　　CPC ............ *C12N 1/20* (2013.01); *A61K 31/7016*
　　　　　(2013.01); *A61K 35/745* (2013.01); *A61K*
　　　　　*2035/115* (2013.01); *C12N 2501/999*
　　　　　(2013.01); *C12R 2001/01* (2021.05)

(58) Field of Classification Search
　　　CPC ............... C12N 1/20; C12N 2501/999; A61K
　　　　　31/7016; A61K 35/745; A61K 2035/115;
　　　　　　　　　　　　　　　　　　　　C12R 2001/01
　　　See application file for complete search history.

(56) References Cited

FOREIGN PATENT DOCUMENTS

| EP | 2289527 | A1 | 3/2011 |
| JP | S63112979 | A | 5/1988 |
| JP | 2011507540 | A | 3/2011 |
| WO | 2007093619 | | 8/2007 |
| WO | 2010003916 | A1 | 1/2010 |
| WO | 2019129808 | | 7/2019 |

OTHER PUBLICATIONS

Duboux et al., "Carbohydrate-controlled serine protease inhibitor (serpin) production in *Bifidobacterium longum* subsp. *longum*." Scientific Reports. 11:7236; 1-16. (Year: 2021).*
Garro et al., "Biological activity of Bifidobacgterium longum in response to environmental pH." Appl Microbiol Biotechnol; 70: 612-617. (Year: 2006).*
Tochio et al., "1-Kestose, the smallest fructooligosaccharide component, which efficiently stimulates Faecalibacterium prausnitzii as well as Bifidobacteria in humans." Foods. 7:140. (Year: 2018).*
"MRS Medium," 2007, downloaded Oct. 29, 2025 and provided as a PDF from < https://www.dsmz.de/microorganisms/medium/pdf/DSMZ_Medium11.pdf> (Year: 2007).*
Wei et al., "Fructose Uptake in Bifidobacterium Longum NCC2705 is Mediated by an ATP-Binding Cassette Transporter", The Journal of Biological Chemistry, vol. 287, Issue No. 1, Jan. 2, 2012, pp. 357-367.
Chinese Office Action for Appl No. 202080047883.5 dated Sep. 28, 2023.
Turroni et al. "Characterization of the Serpin-Encoding Gene of Bifidobacterium breve 210B" Applied and Environmental Microbiology, May 2010, vol. 76, No. 10, pp. 3206-3219.
McCarville et al. "A Commensal Bifidobacterium longum Strain Prevents Gluten-Related Immunopathology in Mice through Expression of a Serine Protease Inhibitor" Applied and Environmental Microbiology, Oct. 2017, vol. 83, issue 19, 13 pages.
Parche et al. "Sugar Transport Systems of Bifidobacterium longum NCC2705" Journal of Molecular Microbiology and Biotechnology, 2007, vol. 12, pp. 9-19.
Schroeder et al. "Bifidobacteria or Fiber Protects against Diet-Induced Microbiota-Mediated Colonic Mucus Deterioration" Cell Host & Microbe, 2018, vol. 23, pp. 27-40.
Pokusaeva et al. "Carbohydrate metabolism in Bifidobacteria" Genes Nutr, 2011, vol. 6, pp. 285-306.
Alsharafani et al. "*Bifidobacterium breve* M4A and *Bifidobacterium longum* subsps. *longum* FA1 Reduced Weight Gain and Hepatic Lipid Droplets in Young Mice Fed High-Fat" Journal of Probiotics & Health, 2016, vol. 4, No. 3, 8 pages.
Challa et al. "Bifidobacterium longum and lactulose suppress azoxymethane-induced colonic aberrant crypt foci in rats" Carcinogenesis, 1997, vol. 18, No. 3, pp. 517-521.
McKellar et al. "Metabolism of fructo-oligosaccharides by *Bifidobacterium* spp." Applied Microbiology and Biotechnology, 1989, vol. 31, pp. 537-541.
Japanese Office Action for Appl No. 2021-576355 dated Jun. 25, 2024, 8 pages.
European Office Action for Appl No. 20 734 759.2-1111 dated Jan. 16, 2026, 7 pages.

* cited by examiner

*Primary Examiner* — Suzanne M Noakes
*Assistant Examiner* — Ciara A McKnight
(74) *Attorney, Agent, or Firm* — K&L Gates LLP

(57)　　　　　ABSTRACT

Use of a fructose disaccharide or fructooligosaccharide, for increasing protein production in *Bifidobacterium longum* subsp *longum*.

12 Claims, 3 Drawing Sheets

SERPIN PRODUCTION

CROSS REFERENCE TO RELATED APPLICATIONS

The present application is a National Stage of International Application No. PCT/EP2020/068400, filed on Jun. 30, 2020, which claims priority to European Patent Application No. 19183653.5, filed on Jul. 1, 2019, the entire contents of which are being incorporated herein by reference.

FIELD OF THE INVENTION

The present invention relates to bacteria expressing serpin, methods for increasing serpin production in bacteria and uses thereof.

BACKGROUND TO THE INVENTION

Gluten-related disorders comprise all diseases triggered by gluten. They include, amongst other pathophysiology, celiac disease and non-celiac gluten sensitivity. Currently, the incidence of a wide spectrum of gluten-related disorders is growing all around the world, especially for celiac disease and non-celiac gluten sensitivity. Both diseases are triggered by ingestion of gluten. Both innate and adaptive immunity are implicated in celiac disease while innate immunity is implicated in non-celiac gluten sensitivity.

A life-long gluten-free diet is the gold standard treatment for celiac disease and non-celiac gluten sensitivity patients, although it may have some limitations on the extraintestinal manifestations of the disease (Sedghizadeh et al., 2002, Oral Surgery, Oral Medicine, Oral Pathology, Oral Radiology, and Endodontology, 94(4), 474-478). It has been shown that following a strict gluten free diet is very difficult as low level cross-contaminations are difficult to avoid and may happen through the whole food production chain, from grains growth to manufacturing processing (Mitchison et al., 1991, Gut, 32(3), 260-265). Furthermore, it has been described that up to 3 g of hidden gluten might be consumed daily under a strict gluten free diet (Aziz et al., 2014, The American journal of gastroenterology, 109(9), 1498).

Celiac disease is prevalent especially in the United States and Europe where around 1% of subjects had positive antibody tests (Dubé et al., 2005, Gastroenterology, 128(4), S57-S67). It is a complex disorder which arises from a complicated interaction among various immunologic, genetic, and environmental factors (Alaedini & Green, 2005). It is triggered by the digestion of wheat gluten and other related cereal proteins such as rye and barley proteins. Symptoms linked with celiac disease are growth retardation, irritability and pubertal delay in children and many gastrointestinal symptoms such as discomfort, diarrhoea, occult stool, steatorrhea and flatulence, (Dubé et al., 2005; Sedghizadeh et al., 2002).

Non-celiac gluten sensitivity (also named non-celiac wheat sensitivity) is an emerging condition. It is defined as a clinical entity induced by the ingestion of gluten leading to intestinal and/or extraintestinal symptoms which could be improved by removing the gluten-containing foodstuff from the diet (Lundin & Alaedini, 2012). In addition to gliadin (the main cytotoxic antigen of gluten), other proteins/peptides present in gluten and gluten-containing cereals (wheat, rye, barley, and their derivatives) may play a role in the development of symptoms. Non-celiac gluten sensitivity is the most common syndrome of gluten-related disorders with prevalence rates between 0.5-13% in the general population (on average 5%) (Catassi et al., 2013, Nutrients, 5(10), 3839-3853).

Serine protease inhibitors (serpin) are a superfamily of proteins found in eukaryotes (Gettins, 2002, Chemical reviews, 102(12), 4751-4804) and prokaryotes (Kantyka et al., Biochimie, 92(11), 1644-1656).

Recently, human serine protease inhibitors have been shown to play an important role in gluten-related disorders. Elafin is human serine protease inhibitor which shows potent inhibitory capacity against various forms of elastases and proteinase (Ying & Simon, 1993, Biochemistry, 32(7), 1866-1874). Elafin is expressed throughout the epithelium of the gastrointestinal tract and its expression and induction is decreased in patients with inflammatory bowel disease and celiac disease (Baranger, Zani, Labas, Dallet-Choisy, & Moreau, 2011; Motta et al., 2012). Recently, elafin has been identified as a substrate for the cross-linking activity of transglutaminase 2 (TG2) (Baranger et al., 2011, PloS one, 6(6), e20976; Motta et al., Science translational medicine, 4(158), 158ra144-158ra144). In-vitro data shows that the addition of elafin moderately inhibits transglutaminase 2 (TG2) thus inhibiting the deamidation of the digestion-resistant 33-mer gliadin peptide, which is one of the potential triggers of the adaptive immune response in celiac disease (McCarville et al. 2015, Current opinion in pharmacology, 25, 7-12).

Delivery of elafin, produced by a recombinant *Lactococcus lactis* has been shown to reduce gluten-induced pathology and normalise intestine inflammation in a mouse model of gluten sensitivity (Galipeau et al., 2014, The American journal of gastroenterology, 109(5), 748-756). However, this proposed therapy is based on a genetically modified microorganism (GMO) and is therefore not compatible with a food application, as consumer acceptance of GMO is very low.

More recently, serpins have been reported in prokaryotes. In silico analysis revealed the presence of genes encoding serpin-like proteins in different *Bifidobacterium* species, particularly in bacteria of the species *Bifidobacterium longum* subsp *longum*. The protein encoded by *B. longum* subsp *longum* (named *B. longum*) NCC 2705 displayed similar antiprotease activity to those of human serpin (Ivanov et al 2006, Journal of Biological Chemistry, 281 (25), 17246-17252).

*B. longum* NCC 2705 was deposited with the Institute Pasteur according to the Budapest Treaty on 29 Jan. 2001 receiving the deposit no. CNCM 1-2618.

It has recently been shown that *B. longum* NCC 2705 (CNCM I-2618), through its serpin production can improve gluten induced pathophysiology in a mouse model of gluten sensitivity, showing its potential as a solution for gluten related disorders (McCarville et al., 2017, Appl. Envoron. Microbiol. Vol. 83, no. 19, e01323-17).

SUMMARY OF THE INVENTION

The present inventors have surprisingly found that fructose disaccharides and fructooligosacharrides (FOS) can increase the production of serpin when added to the growth medium of bacteria of the species *Bifidobacterium longum* subsp *longum*.

Accordingly, in a first aspect of the present invention, there is provided use of a fructose disaccharide or a fructooligosacharride (FOS), or combinations thereof, for increasing serpin production in a *Bifidobacterium longum* subsp *longum*.

In another aspect of the present invention, there is provided a method of increasing serpin production in a bacteria of the species *Bifidobacterium longum* subsp *longum*, wherein said method comprises growing *Bifidobacterium longum* subsp *longum* in a culture medium, characterised in that said culture medium comprises a fructose disaccharide or a fructooligosacharride (FOS), or combinations thereof.

According to another aspect of the present invention, there is provided a bacteria of the species *Bifidobacterium longum* subsp *longum* produced by a method of growing the *Bifidobacterium longum* subsp *longum* in a culture medium, characterised in that said culture medium comprises a fructose disaccharide or a FOS, or combinations thereof.

The *Bifidobacterium longum* subsp *longum* produced according to the present invention is associated with increased serpin protein levels relative to the same *Bifidobacterium longum* subsp *longum* strain grown in the absence of a fructose disaccharide or FOS, or combinations thereof.

According to the present invention, the *Bifidobacterium longum* subsp *longum* may be cultured in a medium comprising the fructose disaccharide or FOS, or combinations thereof, at a concentration of, for example, 0.02 to 5 wt %, preferably 0.05 to 2 wt %.

For example, the *B. longum* strain CNCM I-2618 may be cultured in a medium comprising the fructose disaccharide or FOS, or combinations thereof, at a concentration of 0.02 to 5 wt %, 0.05 to 2 wt %, 0.1 to 1.5 wt %, or about 1%.

In some preferred embodiments the fructose disaccharide is selected from saccharose, lactulose, or combinations thereof. In some preferred embodiments saccharose is used.

In some preferred embodiments the FOS is a short-chain FOS, having an average DP of 2 to 10.

According to another aspect of the present invention, there is provided a composition comprising a *Bifidobacterium longum* subsp *longum* produced according to the method described herein.

In one embodiment, the composition is a food, a medical food, a tube feed, or a nutritional supplement.

In one embodiment, the food is selected from milk, yoghurt, curd, cheese, fermented milks, milk based fermented products, rice based products, milk based powders, infant formulae and pet food.

In one embodiment, the composition is a pharmaceutical composition wherein the pharmaceutical composition comprises one or more pharmaceutically acceptable carriers, diluents and/or excipients.

According to another aspect of the present invention there is provided a *Bifidobacterium longum* subsp *longum* produced according to the method described herein, or a composition comprising said *Bifidobacterium longum* subsp *longum*, for use in the treatment or prevention of conditions related to gluten sensitivity or involving the reduced activity of serine protease inhibitors.

According to another aspect of the present invention there is provided a *Bifidobacterium longum* subsp *longum* produced according to the method described herein, or a composition comprising said *Bifidobacterium longum* subsp *longum*, for use in the treatment or prevention of a gluten-related disorder.

According to an aspect of the present invention there is provided a *Bifidobacterium longum* subsp *longum* produced according to the method described herein, or a composition comprising said *Bifidobacterium longum* subsp *longum*, for use in the treatment or prevention of, celiac disease, non-celiac gluten sensitivity, gluten ataxia, dermatitis herpetiformis or wheat allergy.

According to another aspect of the present invention there is provided a *Bifidobacterium longum* subsp *longum* produced according to the method described herein, or a composition comprising said *Bifidobacterium longum* subsp *longum*, for use in the treatment or prevention of inflammatory bowel disease.

The *Bifidobacterium longum* subsp *longum* may be any *Bifidobacterium longum* subsp *longum* strain. In some preferred embodiments the *Bifidobacterium longum* subsp *longum* strain may be selected from *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), or a combination thereof, in particular *B. longum* CNCM I-2618 (NCC 2705).

In some embodiments the fructose disaccharide is selected from saccharose, lactulose, or combinations thereof. In some preferred embodiments saccharose is used.

In some embodiments the FOS have a DP ranging from 2 to 10, preferably from 2 to 8.

It will also be appreciated that the fructose disaccharide and/or FOS may also increase the production of serpin in *Bifidobacterium longum* subsp *longum* in vivo when the fructose disaccharide or FOS, or a combination thereof, is administered in combination with the *Bifidobacterium longum* subsp *longum*.

Thus, according to another aspect of the present invention there is also provided a combination of (i) a *Bifidobacterium longum* subsp *longum* and (ii) a fructose disaccharide or FOS, or combinations thereof.

According to another aspect of the present invention there is also provided a combination of (i) a *Bifidobacterium longum* subsp *longum* and (ii) a fructose disaccharide or FOS, or a combination thereof, for use in the treatment or prevention of a condition related to gluten sensitivity or a condition linked to reduced levels of serine protease inhibitors.

In one embodiment, the combination is a combination of *B. longum* strain CNCM I-2618 and saccharose.

In another embodiment, the combination is a combination of *B. longum* strain CNCM I-2618 and a FOS, preferably a FOS having a DP ranging from 2 to 10, preferably from 2 to 8.

According to another aspect of the present invention there is also provided *Bifidobacterium longum* subsp *longum* for use in the treatment or prevention of a condition related to gluten sensitivity or a condition linked to reduced levels of serine protease inhibitors, wherein the *Bifidobacterium longum* subsp *longum* is administered in combination with a fructose disaccharide or FOS, or a combination thereof.

According to another aspect of the present invention there is provided a fructose disaccharide or FOS, or a combination thereof for use in the treatment or prevention of a condition related to gluten sensitivity, or a condition linked to reduced levels of serine protease inhibitors, wherein the fructose disaccharide or FOS, or a combination thereof, is administered in combination with *Bifidobacterium longum* subsp *longum*.

In some embodiments the *Bifidobacterium longum* subsp *longum* may be selected from from *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), or a combination thereof.

In some preferred embodiments, the *Bifidobacterium longum* subsp *longum* may be selected from *Bifidobacterium longum* subsp *longum* strain CNCM I-2169, *Bifidobacterium longum* subsp *longum* strain CNCM I-2171, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), or a combination thereof.

In some preferred embodiments, the *Bifidobacterium longum* subsp *longum* strain *B. longum* CNCM I-2618 (NCC 2705) is used.

In some embodiments the fructose disaccharide is selected from saccharose, lactulose, or combinations thereof. In some preferred embodiments saccharose is used.

In some embodiments the FOS have a DP ranging from 2 to 10, preferably from 2 to 8.

DETAILED DESCRIPTION OF THE INVENTION

Composition

Figure 1:
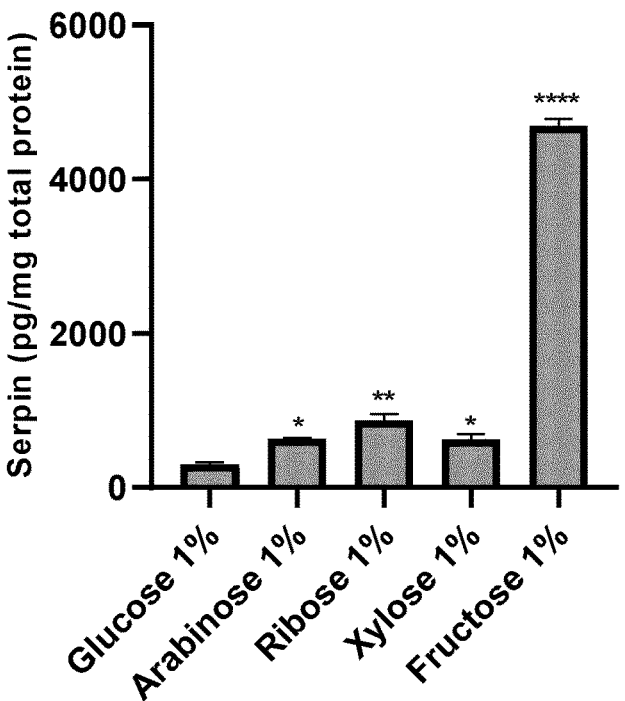
FIG. 1—Shows serpin protein levels measured in *B. longum* NCC 2705 grown for 48 h on different carbohydrates.

The composition of the present invention may be in the form of a food, a medical food, a tube feed, a nutritional composition, or a nutritional supplement. The term "nutritional supplement" refers to a product which is intended to supplement the general diet of a subject.

In one embodiment, the food is selected from milk, yoghurt, curd, cheese, fermented milks, milk based fermented products, rice based products, milk based powders, infant formulae and pet food.

The composition may be in the form of a medical food. The term "medical food" as used herein refers to a food product specifically formulated for the dietary management of a medical disease or condition. The medical food may be administered under medical supervision. The medical food may be for oral ingestion or tube feeding.

The composition may be in the form of a tube feed. The term "tube feed" refers to a product which is intended for introducing nutrients directly into the gastrointestinal tract of a subject by a feeding tube. A tube feed may be administered by, for example, a feeding tube placed through the nose of a subject (such as nasogastric, nasoduodenal, and nasojejunal tubes), or a feeding tube placed directly into the abdomen of a subject (such as gastrostomy, gastrojejunostomy, or jejunostomy feeding tube).

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients", 2nd Edition, (1994), Edited by A Wade and P J Weller. Acceptable carriers or diluents for therapeutic use are well known in the pharmaceutical art, and are described, for example, in "Remington's Pharmaceutical Sciences", Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s) and/or solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption that are used as standard in the food industry. Typical nutritionally acceptable carriers, diluents and excipients will be familiar to the skilled person in the art.

The composition may be in the form of a tablet, dragee, lozenges, capsule, gel cap, powder, granule, solution, emulsion, suspension, coated particle, spray-dried particle or pill.

In an alternative embodiment the composition may be in the form of a composition for topical administration, such as a gel, cream, ointment, emulsion, suspension or solution for topical administration.

It is clear to those skilled in the art that an ideal dose will depend on the subject to be treated, its health condition, sex, age, or weight, for example, and the route of administration. The dose to be ideally used will consequently vary but can be determined easily by those of skill in the art.

However, generally, it is preferred if the composition of the present invention comprises between $10^6$ and $10^{10}$ cfu and/or between $10^6$ and $10^{10}$ cells of *Bifidobacterium longum* subsp *longum* per daily dose. It may also comprise between $10^6$ and $10^{11}$ cfu and/or between $10^6$ and $10^{11}$ cells of *Bifidobacterium longum* subsp *longum* per g of the dry weight of the composition.

Bifidobacterium Longum

The serpin encoding gene and its surrounding is highly conserved within the *B. longum* subsp. *longum* species. The *Bifidobacterium longum* may be any *Bifidobacterium*

*longum* subsp *longum* strain. In some embodiments the *Bifidobacterium longum* subsp *longum* strain may be selected from *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999 (available from Morinaga Milk Industry Co. Ltd, as BB536), *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), *Bifidobacterium longum* subsp *longum* strain CNCM I-103, *Bifidobacterium longum* subsp *longum* strain CNCM I-2334, *Bifidobacterium longum* subsp *longum* strain CNCM I-3864, *Bifidobacterium longum* subsp *longum* strain CNCM I-3853, or a combination thereof.

The strains have been deposited in the depositary institution indicated in the table below (Table 1), and have received the following date of deposit and accession number:

TABLE 1

| # | Depositary institution | Accession number | Date of deposit |
|---|---|---|---|
| 1 | CNCM | I-2169 | 15 Mar. 1999 |
| 2 | CNCM | I-2171 | 15 Mar. 1999 |
| 3 | ATCC | 15708 | <1990 |
| 4 | DSM | 20097 | <1990 |
| 5 | NCIMB | 8809 | 1 Oct. 1956 |
| 6 | CNCM | I-2618 | 29 Jan. 2001 |
| 7 | CNCM | I-2170 | 15 Mar. 1999 |
| 8 | ATCC | 15707 | <1990 |
| 9 | CNCM | I-103 | 29 Oct. 1979 |
| 11 | CNCM | I-2334 | 12 Oct. 1999 |
| 12 | CNCM | I-3864 | 15 Nov. 2007 |
| 13 | CNCM | I-3853 | 16 Oct. 2007 |

CNCM refers to Collection nationale de cultures de micro-organismes, Institut Pasteur, 28, rue du Dr Roux, F-75724 Paris Cedex 15, France. ATCC refers to American Type Culture Collection 10801 University Blvd., Manassas, Virginia 20110-2209, U.S.A. DSM refers to Leibniz Institute DSMZ-German Collection of Microorganisms and Cell Cultures, Inhoffenstr. 7B, D-38124 Braunschweig, Germany. NCIMB refers to NCIMB Ltd, Ferguson Building, Craibstone Estate, Buckburn, Aberdeen AB21 9YA, Scotland.

Strains 1, 2, 6, 7, 9, 11-13 have been deposited by Nestec S.A., avenue Nestlé 55, 1800 Vevey, Switzerland. Since then, Nestec S.A. has merged into Société des Produits Nestlé S.A. Accordingly, Société des Produits Nestlé S.A. is the successor in title of Nestec S.A., under article 2(ix) of the Budapest Treaty. All other strains are commercially available.

In some preferred embodiments, the *Bifidobacterium longum* subsp *longum* may be selected from *Bifidobacterium longum* subsp *longum* strain CNCM I-2169, *Bifidobacterium longum* subsp *longum* strain CNCM I-2171, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), or a combination thereof.

In some preferred embodiments, the *Bifidobacterium longum* subsp *longum* strain *B. longum* CNCM I-2618 (NCC 2705) is used.

Fructose Disaccharides and FOS

The present inventors have surprisingly found that fructose disaccharides and fructooligosaccharides (FOS) can increase the production of serpin in bacteria of the species *Bifidobacterium longum* subsp *longum*.

The term "oligosaccharide" as used herein refers to a carbohydrate having a degree of polymerisation (DP) ranging from 2 to 20 inclusive.

"Degree of polymerisation" or "DP" refers to the total number of saccharide units in an oligo- or polysaccharide chain.

The term "fructose disaccharide" as used herein refers to a disaccharide containing at least one fructose molecule.

Examples of suitable fructose disaccharides include saccharose (composed of one glucose molecule and one fructose molecule), lactulose (composed of one galactose and one fructose molecule), turanose (composed of glucose and one fructose molecule).

The term "fructo-oligosaccharide" (FOS) as used herein refers to a non-digestible oligosaccharide comprising two or more fructose molecules. The fructo-oligosaccharides of the present invention have a DP of 2 to 200, preferably a DP of 2 to 100, from example a DP of 2 to 60, more preferably a DP of 2 to 20 or a DP of 2 to 10. In some preferred embodiments the FOS are short-chain FOS, having a DP ranging from 2 to 10 inclusive, preferably from 2 to 8 inclusive.

Preferably at least 30% of the saccharide units of the FOS are fructose units, preferably at least 60%, more preferably at least 90%, based on monomeric subunits. In some preferred embodiments the FOS are composed of fructose monomeric subunits linked by a beta-1,2-bond, optionally with an end-standing glucose sub unit. Preferably with a DP of from 2 to 8 inclusive.

Because of the configuration of their glycosidic bonds, fructooligosaccharides (FOS) largely resist hydrolysis by salivary and intestinal digestive enzymes. FOS are classified as prebiotics, non-digestible carbohydrates that beneficially affect the host by stimulating the growth and/or activity of beneficial bacteria in the colon.

The *Bifidobacterium longum* subsp *longum* may be cultured in a medium comprising a fructose disaccharide or FOS, or a mixture thereof, at a concentration of, for example, 0.02 to 5 wt %. For example, the *Bifidobacterium longum* subsp *longum* may be cultured in a medium comprising a fructose disaccharide or FOS, or mixtures thereof, at a concentration 0.02 to 5 wt %, 0.05 to 2 wt %, 0.1 to 1.5 wt %, or about 1 wt %.

The fructose disaccharide or FOS, or mixtures thereof, may be added to a conventional culture medium comprising up to 8 wt %, preferably up to 6 wt %, for example up to 4 wt %, of another sugar suitable to sustain *B. longum* growth, such as, but not limited to, glucose. Fructose disaccharides can induce production of serpin in *Bifidobacterium longum* subsp *longum* even when glucose is present. Preferably the culture medium at the end of the fermentation contains less than 0.4 wt % glucose, such as from 0 wt % to 0.3 wt % glucose. Conventional culture mediums suitable for growth of *B. longum* are well known to the person skilled in the art.

In one embodiment, the *Bifidobacterium longum* subsp *longum* may be cultured in a medium comprising a fructose disaccharide or FOS at a concentration of, 0.05 to 2 wt %, 0.1 to 1.5 wt %, or about 1 wt %, optionally in the presence of glucose. Preferably the culture medium at the end of the fermentation contains less than 0.4 wt % glucose, such as from 0 wt % to 0.3 wt % glucose.

In one embodiment, saccharose is used at the concentrations described above.

In one embodiment, FOS is used at the concentrations described above.

Process for Producing a Culture Powder

Strains belonging to the species *B. longum* are grown in anaerobic conditions. Fermentation methods under anaerobic conditions are commonly known. The skilled person is able to identify suitable components of the fermentation medium and to adjust fermentation conditions based on his general knowledge, depending on the microorganism to be grown. The fermentation medium typically comprises a nitrogen source such as yeast extract, a carbon source such as a sugar, various growth factors (e.g minerals, vitamins etc.) required by the microorganism and water.

A non-limiting example of a typical growth medium for *B. longum* is MRS (De Man, Rogosa and Sharpe) medium, supplemented with 0.05% of cysteine (MRSc).

The fermentation is preferably carried out in two steps, a starter fermentation being carried out prior to the main fermentation step. The fermentation medium can be different for the starter and the main fermentation or may be identical.

The second step of the process is the concentration of the biomass. This can also be carried out using methods known to the person skilled in the art, such as for example centrifugation or filtration. The total solid content of the biomass after concentration is preferably comprised between 10 and 35 wt %, preferably between 14 and 35 wt %, based on the total dry weight of the biomass (i.e. of the total amount of fermentation medium and produced microorganism).

Optionally, the concentration may be preceded or combined with a washing step to remove residues of the fermentation medium and/or compounds produced during fermentation. For example, washing may be performed by concentrating biomass, re-suspending the concentrated biomass in a buffer, such as a phosphate buffer, or a similar composition and re-concentrating the biomass.

For example, the process described in WO2017/001590, which is entirely incorporated by reference, can be applied.

Combination

In one aspect of the present invention, there is provided a combination of (i) a *Bifidobacterium longum* subsp *longum* and (ii) a fructose disaccharide or FOS, or a combination thereof.

As used herein, the term "combination" refers to the combined administration of *Bifidobacterium longum* subsp *longum* and a fructose disaccharide or FOS, or a combination thereof, wherein the *Bifidobacterium longum* subsp *longum* and the fructose disaccharide and/or FOS may be administered simultaneously or sequentially.

As used herein, the term "simultaneous" or "simultaneously" is used to mean that the two agents are administered concurrently, i.e. at the same time.

The term "sequential" or "sequentially" is used to mean that the two agents are administered one after the other, wherein either the *Bifidobacterium longum* subsp *longum* or the fructose disaccharide or FOS, or the combination thereof, may be administered first.

The agents may be administered either as separate formulations or as a single combined formulation.

When the compounds are co-formulated, i.e. in the same composition or formulation, they can only be administered simultaneously. When the compounds are formulated in separate compositions or formulations, they can be administered simultaneously or sequentially. Simultaneous administration of the agents in the same formulation or in separate formulations can also be described as the co- or joint administration of the two compounds.

In one embodiment, *Bifidobacterium longum* subsp *longum* and the fructose disaccharide or FOS, or a combination thereof are in admixture. In another embodiment, the *Bifidobacterium longum* subsp *longum* and fructose disaccharide or FOS, or a combination thereof, are present in the form of a kit comprising a preparation of the two agents and, optionally, instructions for the simultaneous or sequential administration of the preparations to a subject in need thereof.

Treatment

The *Bifidobacterium longum* subsp *longum* strains produced according to the present invention, or a composition comprising the same, may be for use in the treatment or prevention of gluten-related disorders or conditions involving a reduced activity of serine protease inhibitors.

For example the *Bifidobacterium longum* subsp *longum* produced according to the present invention, or a composition comprising the same, may be for use in the treatment or prevention of inflammatory bowel disease, celiac disease, non-celiac gluten sensitivity, gluten ataxia, dermatitis herpetiformis and wheat allergy.

Preferably the disease is a gluten-related disorder. Gluten-related disorders encompass diseases triggered by gluten. The terms "conditions related to gluten sensitivity" and "gluten-related disorders" are used interchangeably herein. Gluten-related disorders include celiac disease, non-celiac gluten sensitivity, gluten ataxia, dermatitis herpetiformis and wheat allergy.

Celiac Disease

Celiac disease is one of the most common immune mediated disorders. It is a worldwide condition and is prevalent especially in the United States and Europe where around 1% of subjects had positive antibody tests. Celiac disease is a complex disorder which arises from a complicated interaction among various immunologic, genetic, and environmental factors. It is triggered by the digestion of wheat gluten and other related cereal proteins such as rye and barley proteins. Symptoms linked with celiac disease are growth retardation, irritability and pubertal delay in children and many gastrointestinal symptoms like discomfort, diarrhoea, occult stool, steatorrhea flatulence.

Clinical evidence shows class II human leukocyte antigens (HLA-DQII), which strongly relate with celiac disease pathology, are expressed in about 95% of celiac disease patients. In the intestinal lumen, gluten protein are partially digested, forming proteolytic-resistant 33-mer gluten peptide. After crossing the small intestinal barrier, they are deamidated by transglutaminase 2 (TG2) with negative charges (Sollid, 2000, Annual review of immunology, 18(1), 53-81), which then bind to the positively charged binding sites of HLA-DQ2.5/8 (Dieterich et al., 1997, Nature medicine, 3(7), 797-801). HLA-DQ2.5/8 displaying those specific gluten peptides signals to helper T cells and other immune cells causing further damage in the small intestine. Antibodies against gluten proteins and autoantibodies to connective tissue components (TG2) are also associated with celiac disease progression (Alaedini & Green, 2005, Annals of internal medicine, 142(4), 289-298).

Non-Celiac Gluten Sensitivity

Non-celiac gluten sensitivity (also designated as non-celiac wheat sensitivity) is an emerging condition. It is defined as a clinical entity induced by the ingestion of gluten leading to intestinal and/or extraintestinal symptoms which could be improved by removing the gluten-containing foodstuff from the diet (Lundin & Alaedini, 2012). The pathogenesis of non-celiac gluten sensitivity is not yet well understood. It has been shown that except for gliadin (main cytotoxic antigen of gluten), other proteins/peptides present in gluten and gluten-containing cereals (wheat, rye, barley, and their derivatives) may play a role in the development of symptoms. Non-celiac gluten sensitivity is the most common syndrome of gluten-related disorders with prevalence rates between 0.5-13% in the general population (Catassi et al., 2013, Nutrients, 5(10), 3839-385). The diagnosis of non-celiac gluten sensitivity is made by exclusion of other gluten-related disorders.

Dermatitis Herpetiformis

Dermatitis herpetiformis is a chronic blistering skin autoimmune condition, characterized by the presence of skin lesions that have an extensive and symmetrical distribution, predominating in areas of greater friction, and affecting mainly both elbows, knees, buttocks, ankles, and may also affect the scalp and other parts of the body. The lesions are vesicular-crusted and when they flake off, they evolve to pigmented areas or a chromic and intense burning, itchy and blistering rash.

The age of onset is variable. It may start in children and adolescents but can also affect individuals of both sexes indistinctly at any age of their lives.

People with dermatitis herpetiformis have different degrees of intestinal involvement, ranging from milder mucosal lesions to the presence of villous atrophy.

Wheat Allergy

Gastrointestinal symptoms of wheat allergy are similar to those of celiac disease and non-celiac gluten sensitivity, but there is a different interval between exposure to wheat and onset of symptoms. Wheat allergy has a fast onset (from minutes to hours) after the consumption of food containing wheat and can lead to anaphylaxis.

Gluten Ataxia

Gluten ataxia is a gluten-related disorder. With gluten ataxia, damage takes place in the cerebellum, the balance center of the brain that controls coordination and complex movements like walking, speaking and swallowing. Gluten ataxia is the single most common cause of sporadic idiopathic ataxia. It accounts for 40% of ataxias of unknown origin and 15% of all ataxias.

Gluten ataxia is an immune-mediated disease triggered by the ingestion of gluten in genetically susceptible individuals. It should be considered in the differential diagnosis of all patients with idiopathic sporadic ataxia. The effectiveness of the treatment depends on the elapsed time from the onset of the ataxia until diagnosis. The death of neurons in the cerebellum as a result of gluten exposure of the subject is irreversible.

Early diagnosis and treatment with a gluten free diet can improve ataxia and prevent its progression. Less than 10% of people with gluten ataxia present any gastrointestinal symptom, yet about 40% have intestinal damage. Sensitive markers of gluten ataxia include anti-gliadin antibodies. Immunoglobulin A (IgA) deposits against transglutaminase 2 (TG2) in the small bowel and at extraintestinal sites are proving to be additionally reliable.

Administration

The *Bifidobacterium longum* subsp *longum* or composition described herein are preferably administered enterally.

Enteral administration may be oral, gastric, and/or rectal.

In general terms, administration of the combination or composition described herein may, for example, be by an oral route or another route into the gastro-intestinal tract, for example the administration may be by tube feeding.

In an alternative embodiment administration of the combination or composition described herein may be topical administration.

The subject may be a mammal such as a human, canine, feline, equine, caprine, bovine, ovine, porcine, cervine and primates. Preferably the subject is a human.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1—*B. longum* CNCM I-2618 (NCC 2705)
Serpin Induction by Saccharose

*B. longum* strain CNCM I-2618 (NCC 2705) was grown in Biolector (growth conditions—anaerobic, 37° C.) in MRS+5 mM L-cysteine (MRSc) base without sugar, to which different carbohydrates were added.

48-well microtiter plate with pH sensor and dissolved oxygen (DO) sensor were used to culture the strains in Biolector (m2p-labs Aachen, Germany). It was continuously shaken to prevent bacteria aggregation for 24 h and 48 h. Cultures were harvested by centrifugation and supernatant was removed. Pellet was resuspended in PBS supplemented with halt protease inhibitor (Sigma) and lysed using glassbeads. Lysate containing both soluble and insoluble material was then collected. Total protein content was measured using Pierce BCA kit (Thermofisher) and serpin protein concentration was determined using ELISA.

As shown in FIG. 1, the mono-saccharide fructose was shown to increase *B. longum* NCC 2705 serpin protein levels, as compared to all other sugars tested.

Figure 2:
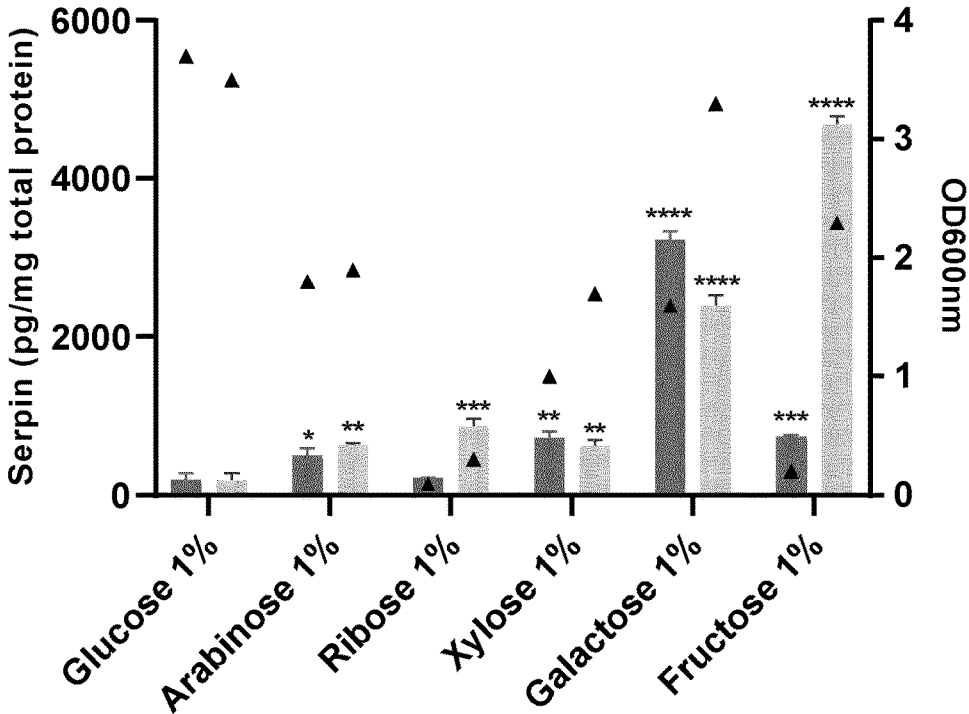
FIG. 2—Shows serpin protein levels measured in *B. longum* NCC 2705 grown on different carbohydrates for 24 h and 48 h.

As shown in FIG. 2 fructose is able to induce serpin in *B. longum* NCC 2705 to a higher magnitude than galactose. However, as the strain takes more time to switch to a fructose based regime, leading to a retarded growth (indicated by triangles, representing culture density measured by Optical Density at 600 nm), the strain needs more time to reach the same levels of serpin protein as compared to when grown on galactose.

Example 2—*B. longum* CNCM I-2618 (NCC 2705)
Serpin Induction by Fructose Disaccharide in the
Presence of Glucose

*B. longum* NCC 2705 was cultured in Biolector (as described in Example 1) in a base of MRSc without sugar, with the addition of different di-saccharides and tri-saccharides, at concentrations of 0.5 wt % and 1 wt %. Cultures were collected after 48 h of growth and analyzed for total & serpin protein levels (as described in Example 1).

Figure 3:
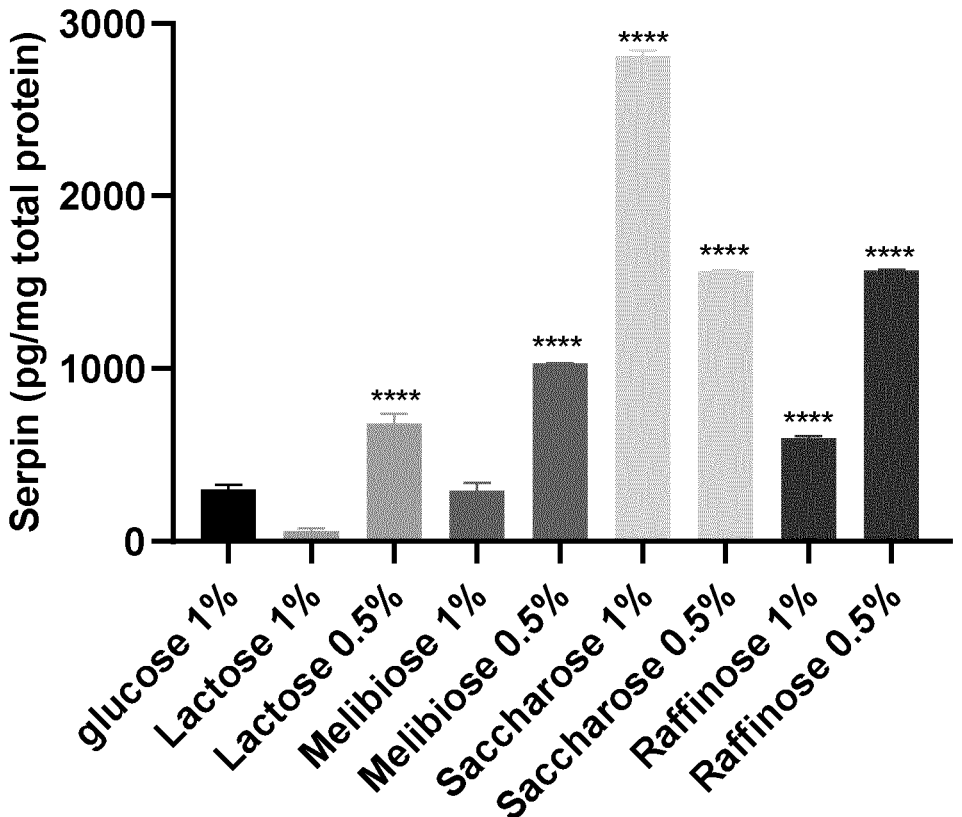
FIG. 3—Shows serpin protein levels measured in *B. longum* NCC 2705 grown on different di- and tri-saccharides for 48 h.

FIG. 3 show that fructose di- and tri-saccharides are able to induce the production of serpin, and to a greater extent than the other di-saccharides tested. For raffinose (tri-saccharide) significant increase in serpin levels was obtained only with a concentration of 0.5 wt %, as compared to a concentration of 1 wt %. Without wishing to be bound by any theory it is supposed that this is due to the presence of high levels of residual glucose at the end of fermentation when the tri-saccharide was used at 1 wt %. Surprisingly it was found that saccharose was able to induce strongly serpin production, even at a 1 wt % concentration.

Example 3—*B. longum* CNCM I-2618 (NCC 2705) Serpin Induction by Short Length Fructo-Oligosaccharides (FOS)

*B. longum* NCC 2705 was cultured in Biolector (as described in Example 1) in a base of MRSc without sugar, with the addition of different short chain fructo-oligosaccharides (FOS), at concentrations of 1 wt %. Cultures were collected after 16 h of growth and analyzed for total & serpin protein levels (as described in Example 1).

The FOS used were (i) NutraFlora P95 FOs from Ingredion Inc, USA., a short-chain FOS with Glucose-Fructose (GF) chains with DP from 3 to 5 and comprising GF2, GF3 and GF4 molecules; (ii) Orafti P95 from Beneo, a short-chain FOS with DP from 2 to 8.

Figure 4:
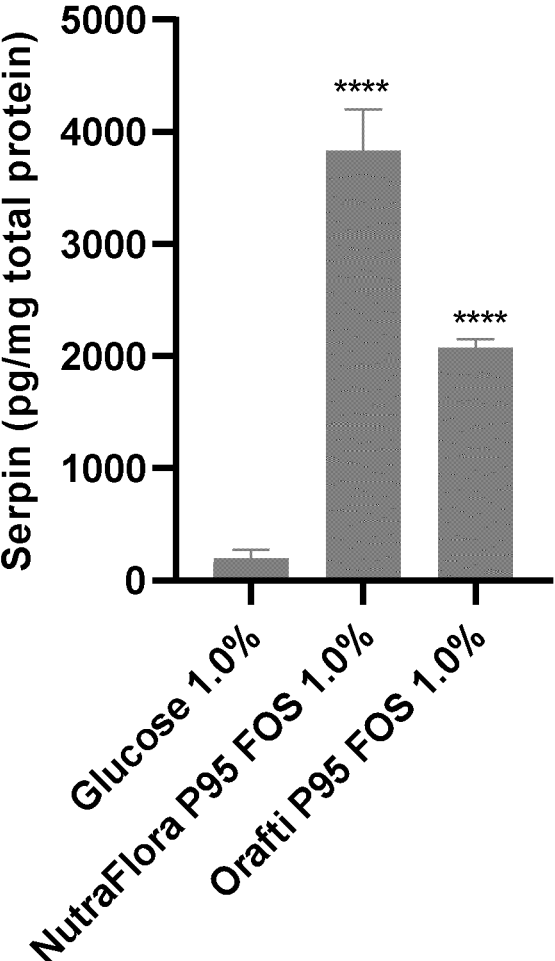
FIG. 4—Shows serpin protein levels measured in *B. longum* NCC 2705 grown on FOS for 16 h

FIG. 4 show that FOS are able to induce the production of serpin, to a greater extend to the glucose grown control.

The invention claimed is:

1. A method for increasing serpin protein levels in *Bifidobacterium longum* subsp *longum*, wherein the method comprises growing the *Bifidobacterium longum* subsp *longum* in a culture medium having a concentration of residual glucose at an end of fermentation that is less than 0.4 wt %, and wherein the culture medium comprises 0.5 to 1.5 wt % of (i) fructose disaccharide or (ii) a combination of fructose disaccharide and fructooligosaccharide (FOS).

2. The method according to claim 1, wherein the culture medium comprises the (i) fructose disaccharide or (ii) a combination of fructose disaccharide and fructooligosaccharide (FOS) at a concentration of 1 wt %.

3. The method according to claim 1, wherein the *Bifidobacterium longum* subsp *longum* is selected from the group consisting of *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), and a combination thereof.

4. The method according to claim 1, wherein the *Bifidobacterium longum* subsp *longum* is *Bifidobacterium longum* strain CNCM I-2618 (NCC 2705).

5. The method according to claim 1, wherein the fructose disaccharide or combination of fructose disaccharide and fructooligosaccharide (FOS) is selected from the group consisting of saccharose, lactulose and a combination thereof.

6. The method according to claim 1, wherein the fructose disaccharide or combination of fructose disaccharide and fructooligosaccharide (FOS) is a FOS having a degree of polymerization (DP) in the range of from 2 to 10.

7. The method of claim 1, further comprising isolating the culture medium after the step of growing the *Bifidobacterium longum* subsp *longum* in the culture medium.

8. The method of claim 1, wherein after the step of growing the *Bifidobacterium longum* subsp *longum* in the culture medium, a biomass is isolated.

9. The method of claim 8, further comprising concentrating the biomass.

10. The method of claim 3, wherein the culture medium comprises up to 8 wt % glucose.

11. The method of claim 1, wherein growing the *Bifidobacterium longum* subsp *longum* comprises a starter fermentation step and a main fermentation step.

12. The method of claim 8, wherein a total solid content of the biomass is between 10 wt % and 35 wt % based on a total dry weight of the biomass.

* * * * *